(12) United States Patent
Foster

(10) Patent No.: US 8,113,348 B2
(45) Date of Patent: Feb. 14, 2012

(54) HYBRID MOUNTING CARDS UTILIZED IN STERILE BARRIER PACKING SYSTEMS

(75) Inventor: Mark James Foster, Doylestown, PA (US)

(73) Assignee: Mangar Industries, Inc., New Britain, PA (US)

(*) Notice: Subject to any disclaimer, the term of this patent is extended or adjusted under 35 U.S.C. 154(b) by 0 days.

(21) Appl. No.: 12/647,837

(22) Filed: Dec. 28, 2009

(65) Prior Publication Data

US 2011/0155608 A1 Jun. 30, 2011

(51) Int. Cl.
*B65D 85/00* (2006.01)
*B65D 73/00* (2006.01)

(52) U.S. Cl. ......... 206/363; 206/370; 206/438; 206/478

(58) Field of Classification Search .......... 206/363–370, 206/438–439, 477–478
See application file for complete search history.

(56) References Cited

U.S. PATENT DOCUMENTS

| | | | | |
|---|---|---|---|---|
| 4,142,632 A | * | 3/1979 | Sandel | 206/363 |
| 4,262,800 A | * | 4/1981 | Nethercutt | 206/364 |
| 5,131,537 A | * | 7/1992 | Gonzalez | 206/364 |
| 5,234,106 A | * | 8/1993 | Transue et al. | 206/363 |
| 5,497,601 A | * | 3/1996 | Gonzalez | 206/364 |
| 5,947,296 A | * | 9/1999 | Castora | 206/438 |
| 6,892,881 B2 | * | 5/2005 | Leitch | 206/364 |
| 6,994,213 B2 | * | 2/2006 | Giard et al. | 206/363 |
| 7,234,597 B2 | * | 6/2007 | Rowe et al. | 206/438 |
| 7,328,794 B2 | * | 2/2008 | Lubs et al. | 206/364 |
| 7,475,776 B2 | * | 1/2009 | Detruit et al. | 206/363 |

* cited by examiner

*Primary Examiner* — Bryon Gehman
(74) *Attorney, Agent, or Firm* — Ryder, Lu, Mazzeo & Konieczny LLC; Douglas J. Ryder

(57) ABSTRACT

A hybrid mounting card is disclosed that includes one or more receptacles form fit for respective portions of a medical device in order to receive and secure the respective portions of the medical device therein and a mounting card adapted to receive and secure the one or more receptacles. The one or more receptacles are configured on the mounting card to secure the medical device to the mounting card in a defined configuration. The use of the receptacles increases the types of medical devices that can be secured to mounting cards. The use of mounting cards enables medical devices to be stored in sterile barrier packaging systems that do not require custom thermoforming of an entire medical tray, such as medical pouches and standard blank medical trays.

18 Claims, 9 Drawing Sheets

HYBRID MOUNTING CARDS UTILIZED IN STERILE BARRIER PACKING SYSTEMS

BACKGROUND

Numerous types of devices are enclosed in packaging of one kind or another. The packaging might range in its purpose and characteristics (e.g., circuit board wrapped in static resistant film, glass vase enveloped in bubble wrap, stereo receiver enclosed in a box). Each of these packaging systems has a desired goal with respect to the package contents. In some cases the packaging is oriented in a certain way so as to display the contents more openly. In other cases the packaging will be primarily to provide protection to the contents.

Some industries have very precise guidelines concerning the types of packaging that can be used to store certain types of goods. Sometimes these packaging systems are very costly to use as tooling cost and materials may require a significant outlay by the manufacturer or packaging producer. Further, changes in product configuration or packaging guidelines may mean that existing packaging may no longer meet the required specifications. The medical device industry requires sterile barrier packaging solutions for single-use Class II and Class III medical devices (or components). The two main types of sterile barrier packaging solutions are medical pouches (pouches) and custom thermoformed medical trays (trays).

FIG. 1 illustrates an example medical pouch 100. The pouch 100 includes two layers secured together with a seal 110 along a majority of the edges and an opening 120 for placing a medical device therein. The seal 110 may be such that any compromises therein are evident to a user so the device can be deposed of if the seal 110 was compromised. One of the two layers may be a clear material that enables a medical device contained therein to be seen. The other material may be a material that enables sterilization to occur (e.g., enables ethylene oxide to pass therethrough). After the medical device is inserted, the opening 120 in the pouch 100 may be sealed using bar sealing equipment and the pouch 100 may be sterilized using any number of known techniques. To remove the medical device from the pouch 100 a user simply pulls the layers of the pouch 100 apart.

The pouches 100 can be designed and produced at a relatively low cost and in a relatively short time frame. The operations required to seal the pouches 100 after the medical device has been inserted therein are relatively easy and low cost. Accordingly, the pouches 100 provide for a cost and operational effective means for providing sterile packaging of medical devices. Furthermore, the space required to store pouch inventory and equipment (bar sealing equipment) as well as the space required for operations (sealing) is relatively small.

However, the use of the pouches 100 is typically limited to certain types of medical devices, including devices and components that are lightweight by design and/or long catheter-type devices. The pouches may not be suitable for medical devices that, for example, have sharp edges that may puncture the pouch if the medical device shifts during transport or need a higher level of structural support.

FIG. 2 illustrates a custom thermoformed medical tray 200. The tray 200 provides a formed fit receptacle 210 within a main body 220 to hold a specific medical device 230. The main body 220 also provides structural support to protect the medical device 230 contained therein. The device 230 securely fits within the receptacle 210 and then a lid (not illustrated) is placed over the tray 200 and sealed thereon using sealing equipment. The lid may be sealed to the tray 200 along the edges 240 of the tray 200. To remove the device 230, the lid is removed from the tray 200 and the device is extracted from the receptacle 210. The design and production of the trays 200 may be relatively expensive and time consuming as it may require extensive prototyping, may require a relatively large amount of material (e.g., plastic) that needs to be tooled, and may require a user to implement a more costly batch production assembly method as changes in product mix may require different trays and tooling for continued packaging operations.

Furthermore, sealing the lids on the trays 200 may be relatively complex and time consuming (more complex and time consuming then the process for sealing pouches). For example, during the lid sealing procedure the lids may be prone to misplacement or having the device stuck in the seal areas. The additional complexity in the sealing process for the trays 200 may result in a relatively large amount of maintenance (more maintenance then for the pouches 100). Moreover, the space required to store the tray inventory and equipment (sealing equipment) as well as the space required for operations (sealing) may be relatively large (more space required then for pouches).

Accordingly, there is a tradeoff between the cost and logistical advantages of the pouches 100 and the structural advantages of the trays 200. Some devices require trays 200 such as devices that are heavier or have a higher profile. However, there are devices that utilize the trays simply because they cannot be used with the pouch 100 and there is no real alternative other that the tray 200.

FIG. 3 illustrates a block diagram of current medical device packaging spectrum 300. On one end of the spectrum 300 there are medical devices typically packaged within pouches 310. On the other end of the spectrum there are those devices that need to be packaged in the trays 330. In the middle of the spectrum are devices that utilize the trays but do not require the trays 320. Devices included in this part of the spectrum include cannula, trocar, catheter and many other devices.

Alternative packaging systems are needed for the devices within the middle of the spectrum 320. The alternative packaging systems should provide a sterile barrier solution with at least some of the cost and logistical advantages of the pouches 100 and at least some of the structural advantages of the trays 200.

SUMMARY

Mounting cards may be used to secure a medical device thereto where the mounting card may be larger then the device and have various tabs and/or folds formed therein to hold the medical device to the card. The mounting card may secure the medical devices such that the device may not damage the pouch. This enables the device to be packaged in medical pouches and thus provide a low cost option for sterile packaging of these devices. The types of devices that can be secured within the tabs and/or folds may be limiting and may require some level of skill to mount the devices.

A hybrid mounting card may replace the tabs and/or folds with one or more receptacles (e.g., thermoformed pieces that will accept a portion of the device) where the mounting card is adapted to receive the one or more receptacles. The hybrid-mounting card may be designed, prototyped, tested, and produced for much less expense and have a much quicker turnaround time then conventional medical trays. The hybrid-mounting card may provide the cost and logistical advantages of the pouches and the structural advantages of the trays. The hybrid-mounting card combines the snug fit advantages of tray solutions with the low cost of mounting cards. The hybrid mounting card solution significantly improves the ease of loading and unloading the medical device onto a mounting card. The hybrid mounting card solutions may be inserted into pouches and extend the types of devices that pouches can be used for.

Neither the mounting card nor the hybrid mounting cards utilized within the pouch provides a packaging solution having the side strength provided by custom trays. Utilizing the mounting cards with blank trays having certain defined sizes (Universal trays) may provide the side support of a custom tray without the cost. The mounting cards utilized in Universal trays may provide the benefits of the "snug fit" and side-strength of a custom thermoformed tray with the low tooling cost advantage of a non-tray solution.

BRIEF DESCRIPTION OF THE DRAWINGS

The features and advantages of the various embodiments will become apparent from the following detailed description in which.

DETAILED DESCRIPTION

Certain medical devices are packaged in custom thermoformed trays because pouches are not an option because if the devices shifted in transport the device could damage the pouch. These devices could possibly be packaged in a pouch if the device was secured in some fashion so that the device could not damage the pouch. For example, if a medical device having a sharp point was secured to a mounting card so that sharp point was not near an edge of the card. The mounting card, with device attached thereto, could then be installed in a pouch.

The mounting card may be larger then the device and have various tabs and/or folds formed therein to hold the medical device to the card. The mounting card may be made of a moldable material (e.g., high-density polyethylene). The mounting card may be prototyped by cutting the moldable material to the appropriate size and then cutting and/or folding the material to achieve the desired configuration of the mounting card and the desired hold. The cutting and/or folding of the prototype may be done manually or a prototype design may be generated in software and the software may instruct, for example, a die cutter to make the appropriate cuts and/or crease the material at the appropriate points to form the folds. Once a prototype design is finalized, the mounting cards may be produced in appropriate quantities by, for example, using a die cutter to cut large pieces of material into a plurality of mounting cards.

The cost of the material that the mounting card are made of may be relatively inexpensive. The design of the tabs and/or folds may be relatively easy and fast, as it does not require any molds to be created. The fabrication of the custom mounting cards may be relatively easy, cheap and fast. The installation of the medical device onto the mounting card using the tabs and/or folds may require some level of mechanical ability to configure the tabs/folds and secure the device thereto. The mounting card and device can be inserted into the pouch. The use of the mounting card can extend the types of medical devices that may be inserted in pouches. However, the types of medical devices that can be mounted to the mounting cards may be limited. That is, it may be difficult to design tabs and/or folds to secure large, heavy, or awkward shaped medical devices.

To increase the types of medical devices that can be secured to mounting cards, small thermoformed pieces may be designed to receive the medical device at various locations and the mounting cards may be designed to secure the small thermoformed pieces thereto. The combination of the mounting card and small thermoformed pieces (hybrid mounting card) may then be capable of securing a wider variety of medical devices.

Figure 1:
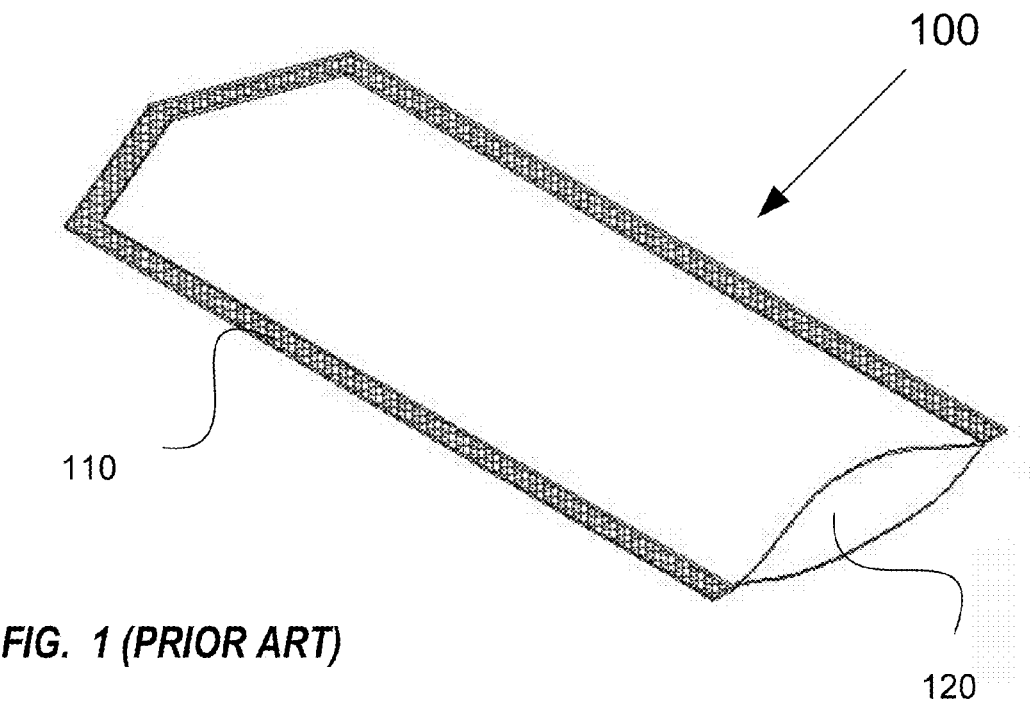
FIG. 1 illustrates an example medical pouch.
Figure 2:
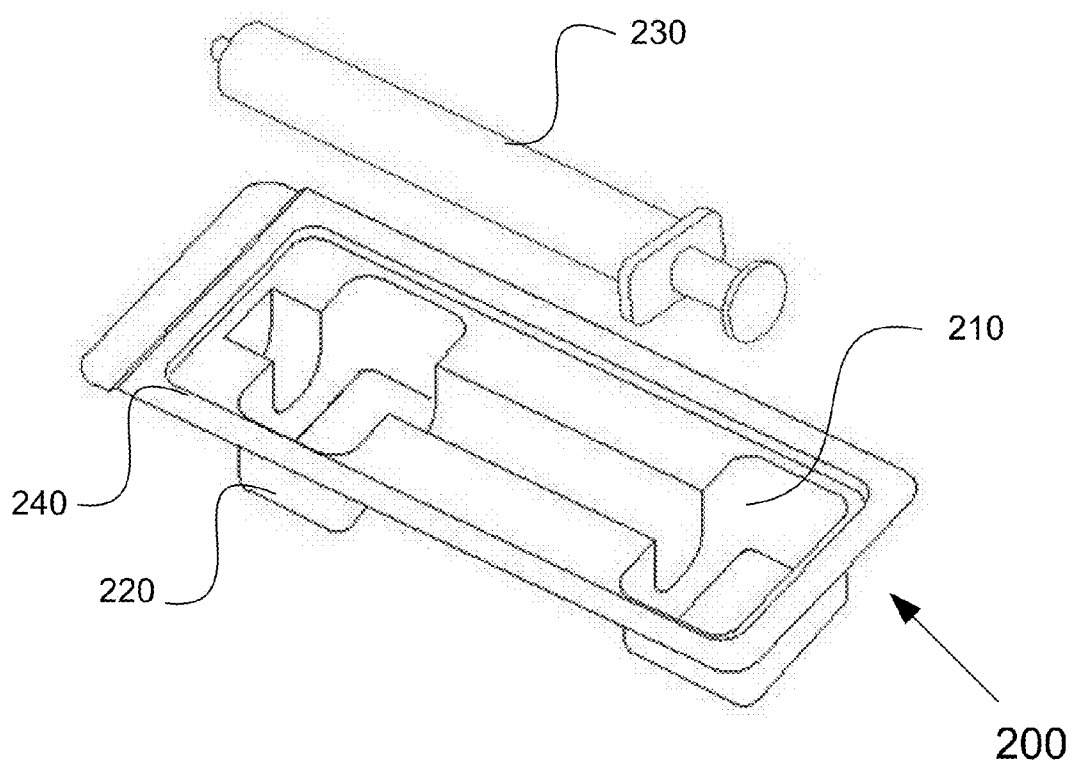
FIG. 2 illustrates an example custom thermoformed medical tray.
Figure 3:
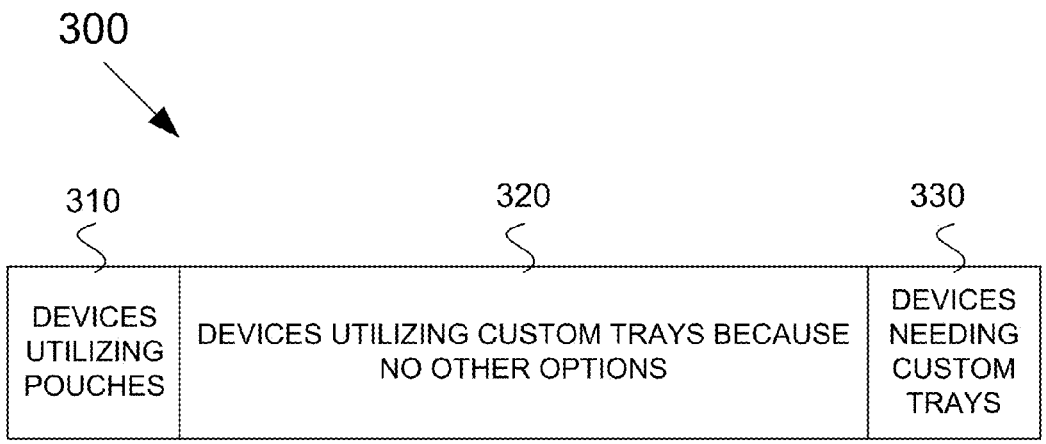
FIG. 3 illustrates a block diagram of current medical device packaging spectrum.
Figure 4A:
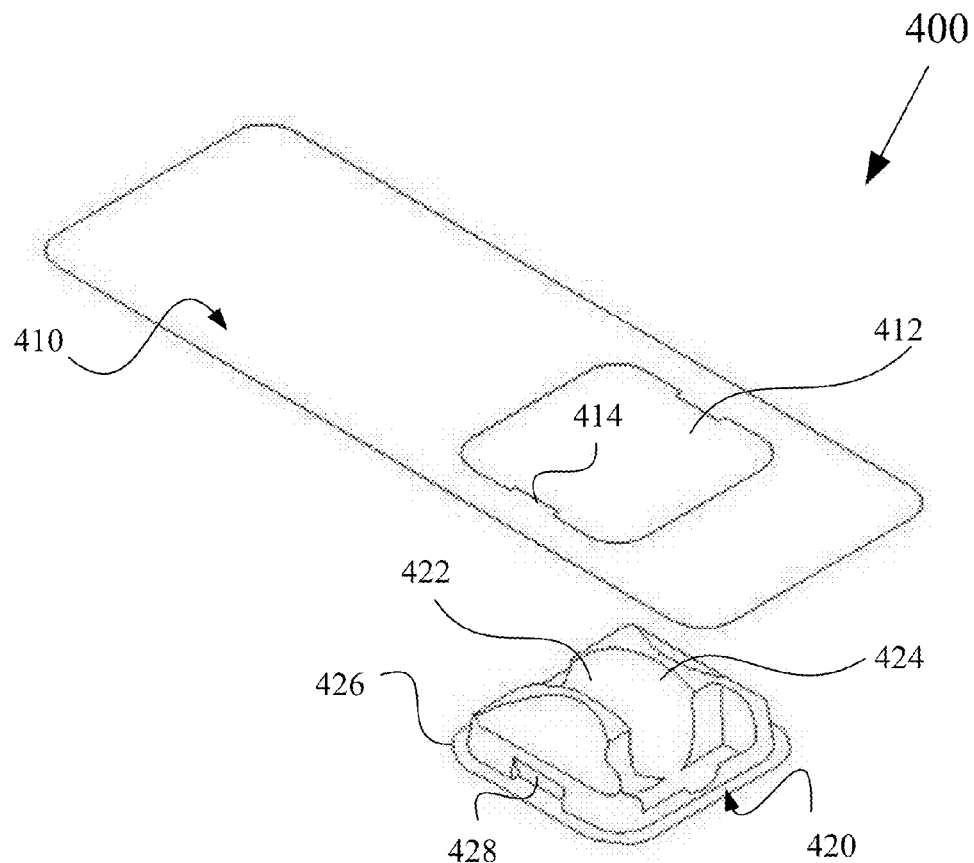
FIGS. 4A-C illustrate several views of an example hybrid mounting card used to secure a medical device thereto, according to one embodiment.
Figure 4B:
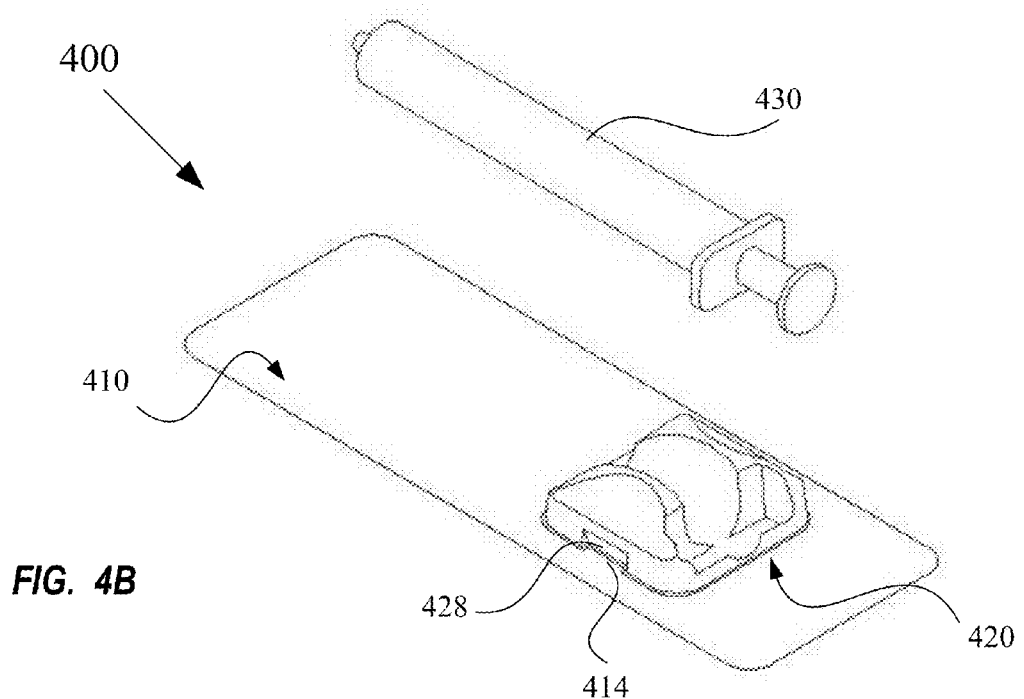
Figure 4C:
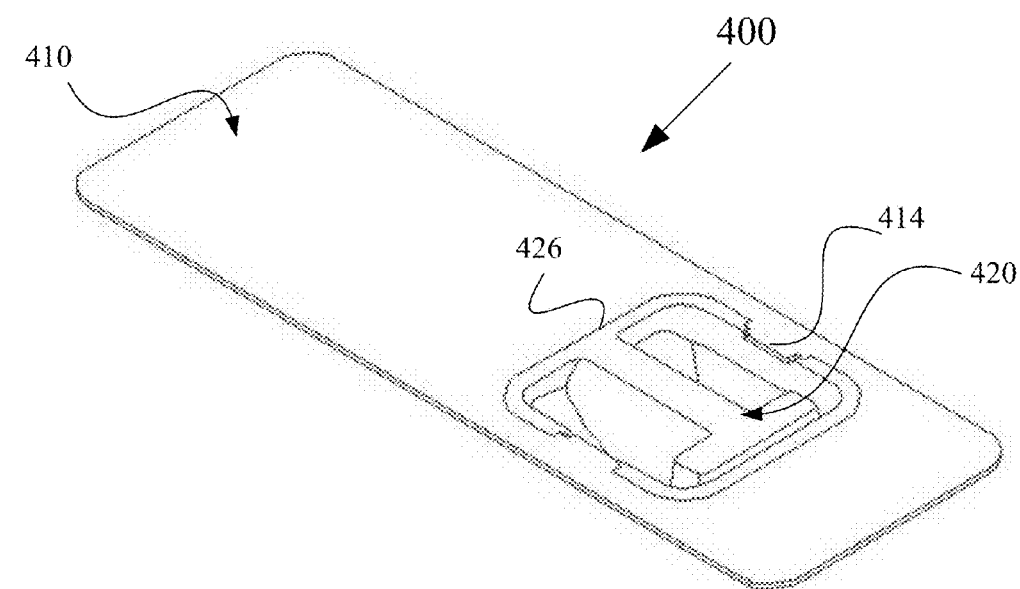

FIGS. 4A-C illustrate several views of an example hybrid mounting card 400 used to secure a medical device 430 thereto. FIG. 4A illustrates an exploded view of the hybrid mounting card 400. The hybrid mounting card 400 may include one or more small thermoformed pieces 420 (receptacles, mini-formers) and a mounting card 410 adapted to receive the one or more receptacles 420 (one illustrated). The receptacles 420 may be used to accept and secure portions of the device. The number and size of the receptacles 420 may be determined based on the device to be mounted to the card 400. The receptacles 420 may include a recessed portion (channel) 422 that the device (or portion thereof) fits within. The size, shape and depth of the channels 422 may be based on the parameters of the device. The receptacles 420 may be made of a flexible material so that sidewalls 424 of the channel 422 flex out when pressure is applied to insert the device in the channel 422. When the device is within the channel 422 the sidewalls 424 may flex back and provide pressure on the device to secure the device therein. When pressure is applied to remove the device the sidewalls 424 may flex out to enable removal of the device.

The mounting card 410 may include openings 412 to receive the receptacles 420. The location of the openings 412 may be based on how the device is to be configured on the hybrid-mounting card 400 and where the device is to be secured (where the pressure points are). The receptacles 420 may include a lip 426 formed along a lower edge. Indents 428 may be formed in the receptacles 420 above the lip 426 (or possibly be formed in the lip 426). The openings 412 may have tabs 414 formed therein that are in alignment with the indents 428. The receptacles 420 may be secured to the mounting card 410 by passing an upper portion of the receptacle 420 through the opening 412 and having the lip 426 abut a lower surface of the mounting card 410. The tabs 414 may enter the indents 428 to secure the receptacle 420 to the mounting card 410. The tabs 414 may flex up as an upper portion of the receptacle 420 passes therethough until the indents 428 are reached at which point the tabs 414 may enter thereinto.

In an alternative embodiment, where the indent 428 are formed in the lip 426, the receptacle 420 may be adjusted within the opening 412 so that the tabs 414 can be pushed below the lip 426 at the indents 428. The receptacle 420 may then be adjusted within the opening 412 so that the tabs 414 push up against the indents 428 from below to hold the lip 426 against the lower surface of the receptacle 420 to the mounting card 410.

FIG. 4B illustrates a perspective view of the top of the example hybrid mounting card 400 ready to receive the medical device 430. The receptacle 420 is inserted in the opening 412 in the mounting card 410 and the tabs 414 entered the indents 428 to secure the receptacle 420 to the mounting card 410. The medical device 430 may be inserted into the receptacle 420 such that the receptacle 420 holds the appropriate portion of the medical device 430 and the medical device 430 is contained on the card 410.

FIG. 4C illustrates a perspective view of the bottom of the example hybrid mounting card 400 (alternative embodiment where the indents 428 are formed in the lip 426). The receptacle 420 has been passed through the opening 412 in the mounting card 410 so that the lip 426 is resting against the lower surface of the mounting card 410. The tabs 414 may be below the lip 426 and pushing up on the indents 428 from below to hold the lip 426 against the lower surface and secure the receptacle 420 to the mounting card 410.

It should be noted that affixing the receptacle 420 within the opening 412 is not limited to the use the tabs 414 and indents 428 as illustrated in FIGS. 4A-C. Rather any means for securing the receptacle 420 within the opening 412 is within the current scope. For example, the opening 412 may have indents formed therein, the lip 426 may have tabs, and the tabs may pass through the indents and then push down on the mounting card 410 to hold the mounting card 410 to the lip 426. By way of another example, there may be no tabs or indents in the lip 426 or opening 412 used to secure the lip 426 to the lower surface of the mounting card 410. Rather, some type of adhesive, and/or connectors may be used secure the lip 426 to the lower surface of the mounting card 410.

It should be noted that affixing the receptacle 420 to the mounting card 410 is not limited to the use of the opening 412. Rather any means for securing the receptacle 420 to the mounting card 410 is within the current scope. For example, the mounting card 410 may include slits or grooves formed therein for receiving the lip of the receptacle 420.

Figure 4D:
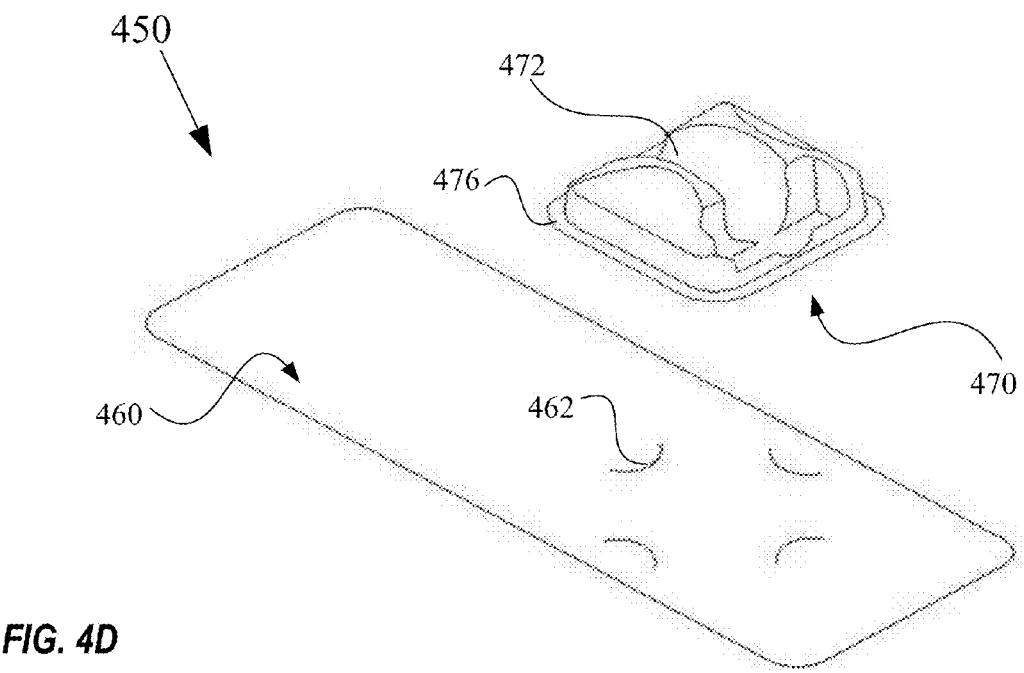
FIGS. 4D-E illustrate several views of an example hybrid mounting card used to secure a medical device thereto, according to one embodiment.
Figure 4E:
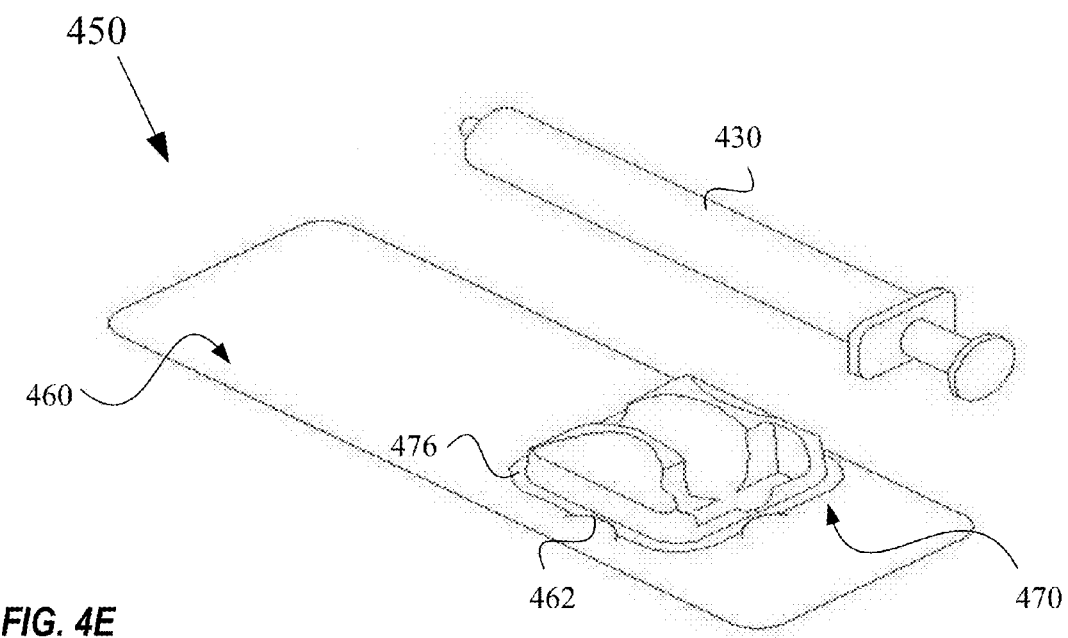

FIGS. 4D-E illustrate several views of an example hybrid mounting card 450 used to secure a medical device 430 thereto. FIG. 4D illustrates an exploded view of the hybrid mounting card 450. The hybrid mounting card 450 may include or more small thermoformed pieces 470 (receptacles, mini-formers) and a mounting card 460 adapted to receive the one or more receptacles 470 (one illustrated). The receptacles 470 may be similar to the receptacles 420 and include a recessed portion (channel) 472 that the device (or portion thereof) 430 fits within, and a lip 476 formed along a lower edge. The mounting card 460 may include slots 462 formed therein for receiving the lip 476 of the receptacle 470.

FIG. 4E illustrates a perspective view of the top of the example hybrid mounting card 450 ready to receive the medical device 430. The receptacle 470 is placed on top of the mounting card 460 and the lip 476 is inserted into the slots 462 to secure the receptacle 470 to the mounting card 460. The medical device 430 may be inserted into the receptacle 470 such that the receptacle 470 holds the appropriate portion of the medical device 430 and the medical device 430 is contained on the card 460.

It should be noted that affixing the receptacle 470 to the mounting card 460 is not limited to the use the slots 462 and lip 476 as illustrated in FIGS. 4D-E. Rather any means for securing the receptacle 470 to the mounting card 460 is within the current scope. For example, some type of adhesive, and/or connectors may be used secure the lip 476 to the upper surface of the mounting card 460.

The receptacles 420, 470 may be designed using computer aided design (CAD) software. Since the designs are relatively small, molds may be fabricated for the receptacles with a much lower cost than larger molds for custom medical trays, and in a relatively quicker time frame. The mold may be used to check the design or the mold may be used to fabricate prototype receptacles (e.g., by thermoforming using the mold) and the prototype receptacles may be used to check the design. The prototype receptacle may be tested to ensure that it provides the desired snug fit for the device 430. The prototype receptacle may also be tested to ensure that it can be secured to the mounting card correctly.

The mounting cards 410, 460 may be designed using CAD software and a prototype may be created utilizing, for example, a die cutter to cut card stock to the appropriate size and to include the appropriate means to receive the receptacles (e.g., openings, slits) based on the CAD design. The prototype mounting cards may be made in a relatively short time frame and for a relatively low cost. The prototype mounting cards may be tested to ensure that the prototype receptacle fits securely therein.

The prototype receptacles and prototype mounting cards may be configured to create the prototype hybrid-mounting card to ensure that the overall design layout effectively supports the device. Once the prototype hybrid-mounting card has been validated and the design is finalized, the receptacles 420, 470 and the mounting cards 410, 460 may be produced. To produce the receptacles 420, 470 a plurality of production molds (either for the same receptacle or different receptacles) may be made so that a plurality of receptacles can be thermoformed from a single sheet of material.

The hybrid-mounting card 400, 450 combines the snug fit advantages of tray solutions with the low cost of mounting cards while improving the ease of loading and unloading the medical device onto a mounting card. The hybrid mounting cards can be designed, prototyped, tested, and produced for much less expense and have a much quicker turn-around then conventional trays. The hybrid mounting cards may be inserted into pouches and extend the types of devices that pouches can be used for.

Figure 5A:
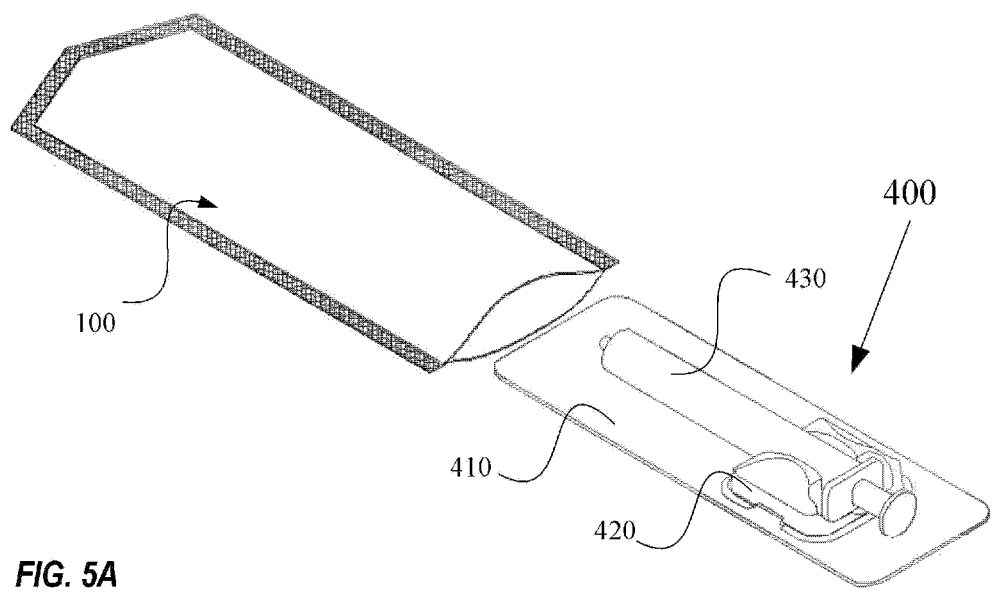
FIGS. 5A-B illustrate comparison perspective views of an example medical device mounted to hybrid mounting card being inserted in a medical pouch and the same example medical device inserted in a custom thermoformed tray, according to one embodiment.

FIG. 5A illustrates a perspective view of the example hybrid mounting card 400 being installed in a pouch 100. By using the hybrid mounting card 400 to secure the device 430, the device 430 that typically would not be installed within the pouch 100 because, for example, the possibility of damaging the pouch 100 may be installed within the pouch 100.

Figure 5B:
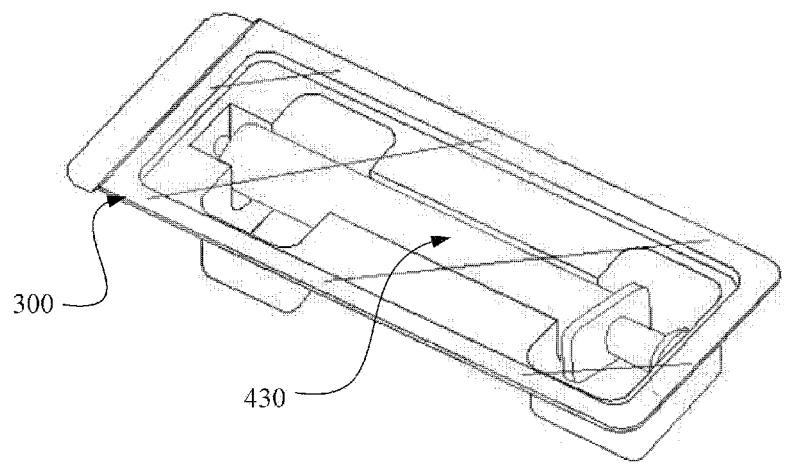

For comparison purposes, FIG. 5B illustrates a perspective view of the device 430 inserted in a thermoformed tray 300. The tray 300 includes much more material and much more customization to secure the device 430. Additionally, as previously noted sealing the lid to the tray 300 is more complicated then sealing the pouch 100.

The size and type of receptacles that can be designed to secure devices is virtually limitless. Rather than designing a large receptacle to secure a device (e.g., like a tray), small receptacles may be designed to secure the device at various pressure points. The receptacles may be oriented on the mounting card to provide the receptacles (pressure points) at the appropriate locations based on the configuration of the device.

Figure 6A:
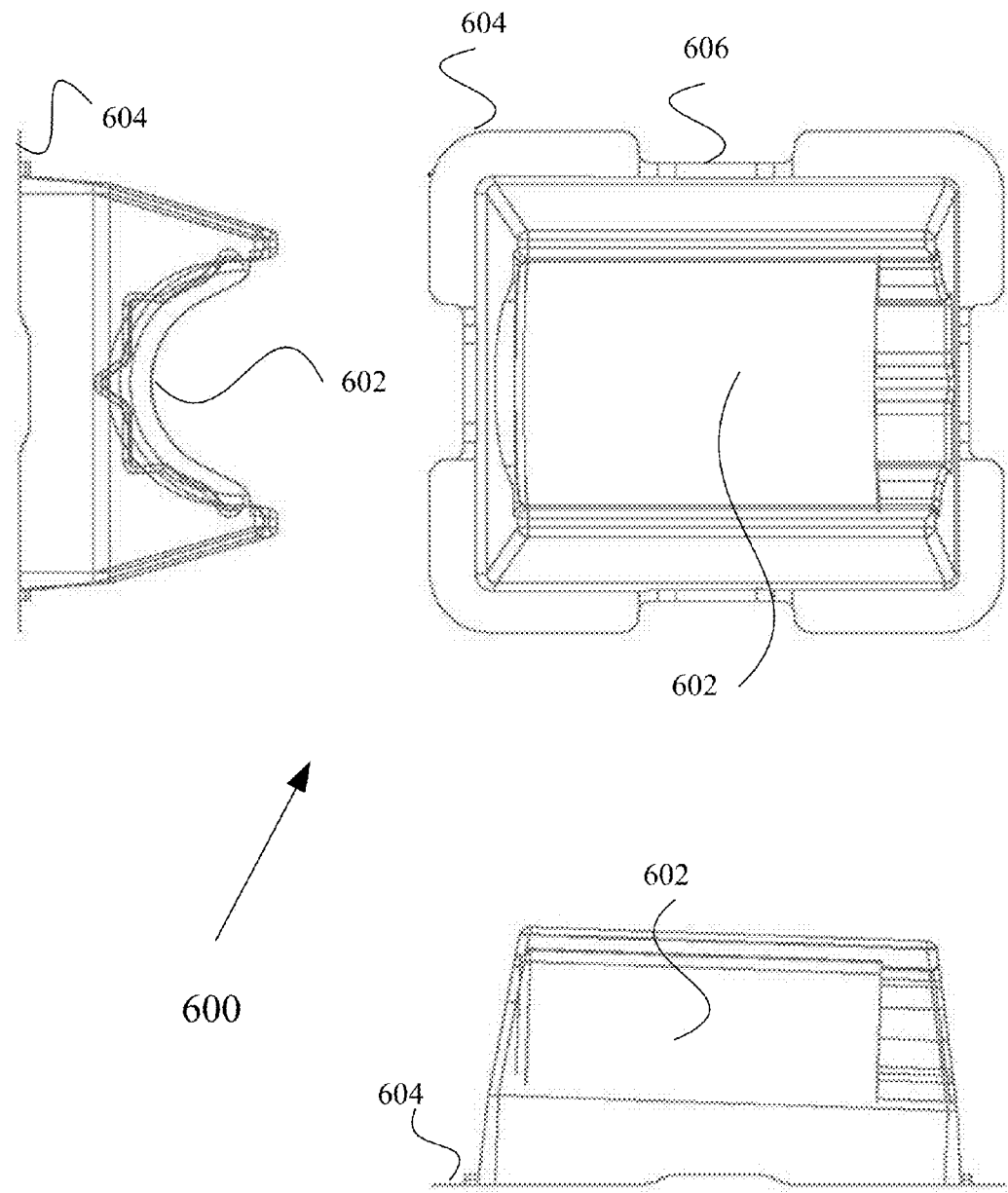
FIGS. 6A-C illustrate various view of example receptacles, according to one embodiment.
Figure 6B:
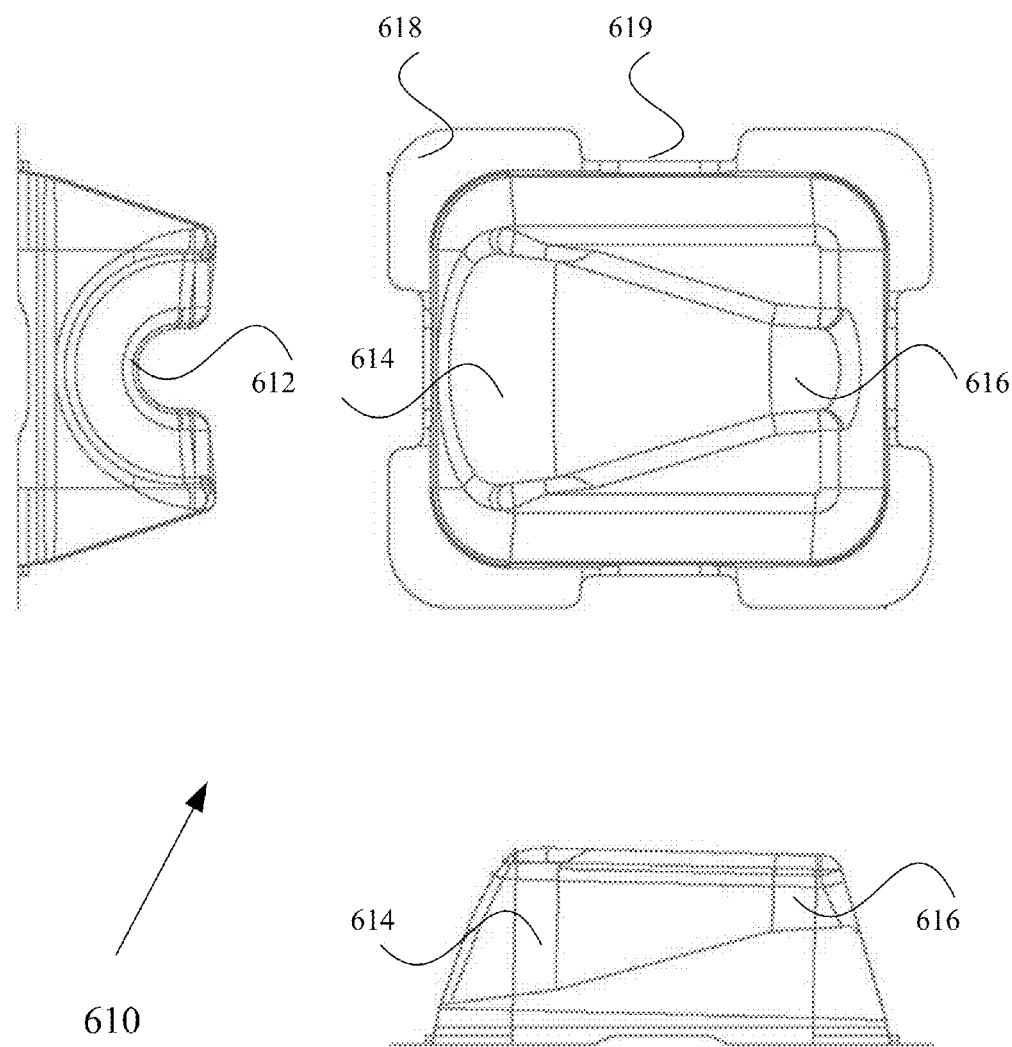
Figure 6C:
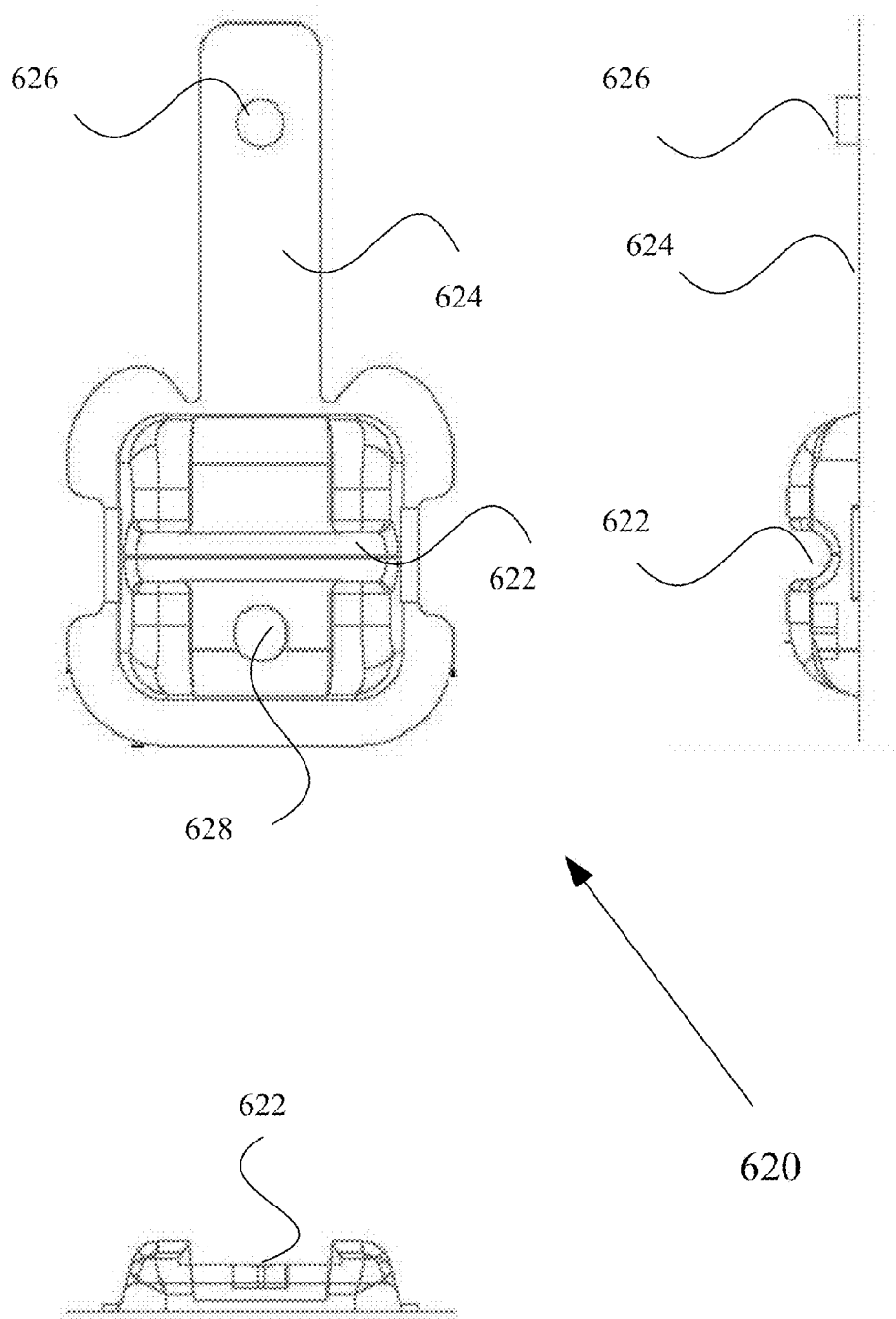

FIGS. 6A-C illustrate various view of example receptacles. FIG. 6A illustrates various views on an example receptacle 600 that includes a groove 602 (e.g., rather large) formed all the way through the receptacle 600. This type of receptacle 600 may be used for supporting the middle portion of a device (the device extends from both sides of the receptacle 600). As illustrated the receptacle 600 includes a lip 604 formed along a lower edge and the lip 604 has indents 606 formed therein.

FIG. 6B illustrates various views on an example receptacle 610 that includes a trough 612 formed therein. The trough 612 may include a first end that is wider and deeper 614 and a second end that is narrower and shallower 616. The first end 614 may be closed while the second end 616 may be open to enable a device to extend therefrom. The receptacle 610 may include a lip 618 formed along a lower edge and the lip 618 may have indents 619 formed therein. This type of receptacle 610 may be used for supporting an end of a device where the very end includes a larger and wider section.

FIG. 6C illustrates various views on an example receptacle 620 that includes a channel 622 formed therethrough. The receptacle 620 also includes a strap 624 that extends therefrom that includes a snap 626 near the end and the body includes an insert 628 to receive the snap 626. The use of the strap 624 enables the device to be further secured therein. This type of receptacle 620 may be used when the channel 622 does not provide pressure on the device at that point. For example, if the device included a portion that was looped around this type of receptacle 620 could be utilized to secure the portion.

While the mounting cards enable pouches to be utilized for devices that they normally would not be able to, the pouches still may not be used for devices that require the side support provided by the trays. However, some devices that require the side support provided by trays do not need to be packaged in custom trays.

The mounting cards 400, 450 could be utilized in blank trays (no special fabrication to house components, simply the shell) where the mounting cards provide the support for the device and the standard trays provide the side support. The blank trays could come in standard sizes (Universal trays) and the mounting cards could be configured to fit with the various standard sizes. The mounting cards may include sidewalls to keep the mounting card, and the device secured thereto, from shifting around within the tray. The mounting card may be placed within the tray so that the bottom of the mounting card abuts the top of the tray and the device faces the opening in the tray. The tray may then be sealed so the device is not visible prior to opening the Universal tray.

According to one embodiment, the device will be inserted within the Universal tray so that the device can be seen from the front of the tray (provide a nice presentation). As the mounting card would likely block a substantial portion of the opening in the Universal tray the mounting card may need to be fabricated in such a fashion as to enable sterilization to occur. This may include providing openings on the sidewalls or the main body of the mounting cards.

Figure 7A:
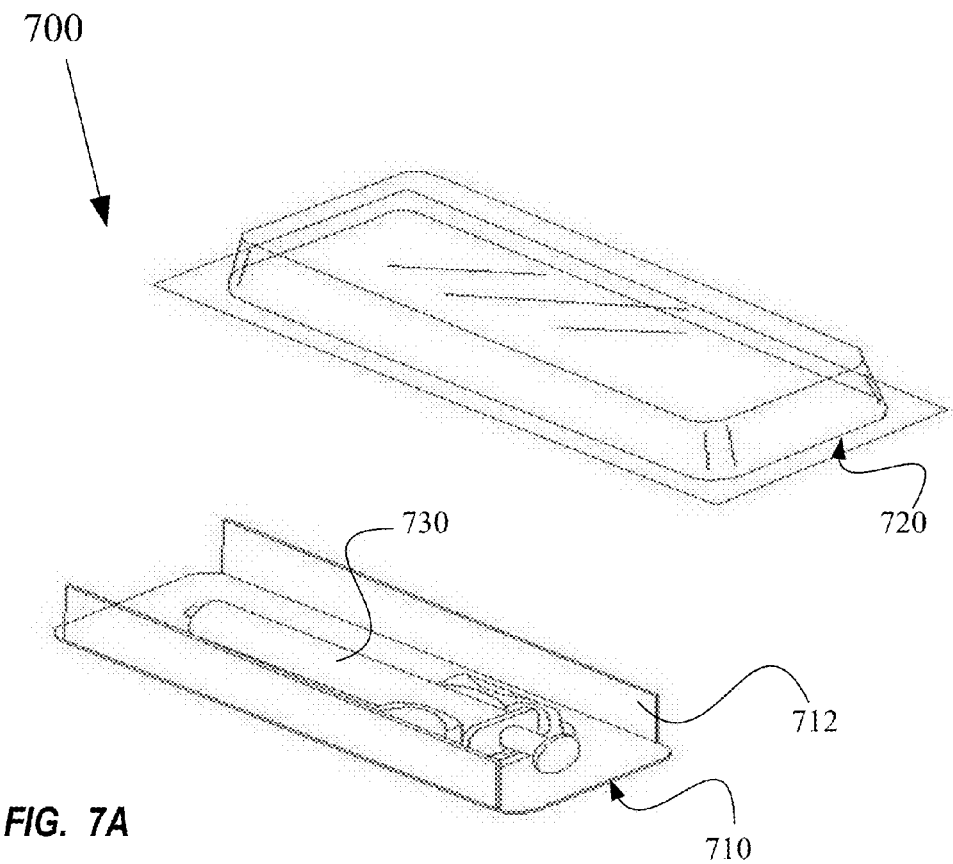
FIGS. 7A-B illustrate several views of a Universal tray packaging system, according to one embodiment.
Figure 7B:
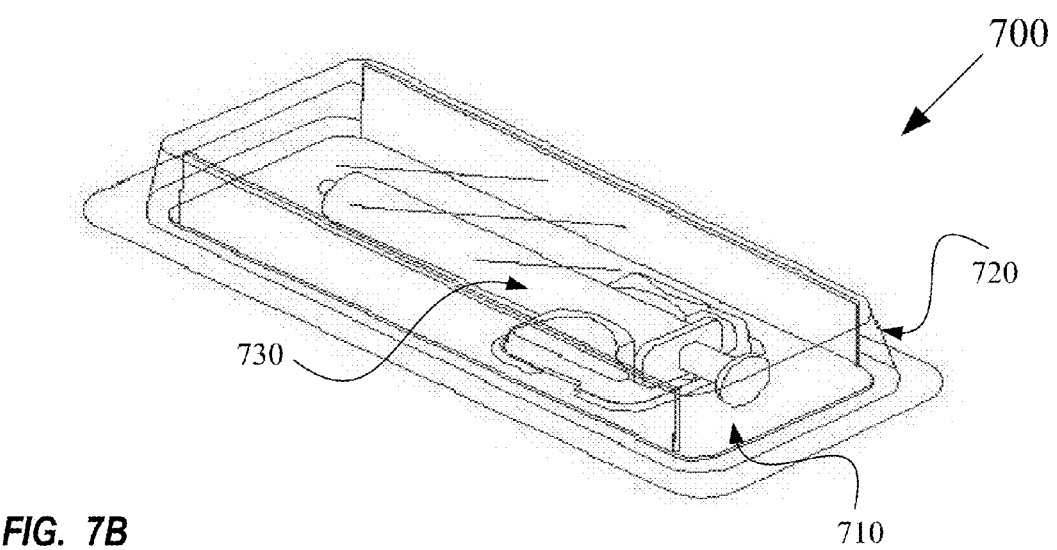

FIGS. 7A-B illustrate several views of a Universal tray packaging system 700. FIG. 7A illustrates an exploded view of the Universal tray packaging system 700. The system 700 includes a Universal tray 720 and a hybrid-mounting card 710 (e.g., 400, 450) having sidewalls 712. The device 730 is mounted to the card 710 between the sidewalls 712. FIG. 7B illustrates a perspective view of the system 700 assembled. The device 730 is mounted to the mounting card 710 and the universal tray 720 is secured over the mounting card 710 and device 730.

Although the disclosure has been illustrated by reference to specific embodiments, it will be apparent that the disclosure is not limited thereto as various changes and modifications may be made thereto without departing from the scope. Reference to "one embodiment" or "an embodiment" means that a particular feature, structure or characteristic described therein is included in at least one embodiment. Thus, the appearances of the phrase "in one embodiment" or "in an embodiment" appearing in various places throughout the specification are not necessarily all referring to the same embodiment.

The various embodiments are intended to be protected broadly within the spirit and scope of the appended claims.

The invention claimed is:

1. A sterile barrier packaging system comprising
one or more receptacles, wherein each of the one or more receptacles is form fit for a respective portion of a medical device, wherein each of the one or more receptacles is to receive the respective portion of the medical device and secure the respective portion of the medical device therein, wherein the one or more receptacles are thermoformed receptacles that include one or more sidewalls, wherein the one or more sidewalls flex apart when pressure is applied to enable the respective portion of the medical device to be received therein and retract back once the respective portion is received to secure the respective portion therewithin;
a mounting card adapted to receive and secure the one or more receptacles, wherein the one or more receptacles are configured on the mounting card to secure the medical device to the mounting card in a defined configuration; and
a sterile barrier to house the mounting card and the medical device.

2. The system of claim 1, wherein the one or more receptacles are to secure the medical device at various pressure points.

3. The system of claim 1, wherein the mounting card includes one or more openings formed therein to receive the one or more receptacles.

4. The system of claim 1, wherein the mounting card includes slots and the one or more receptacles each include a lip and the lip is secured within the slots.

5. The system of claim 1, wherein the sterile barrier is a medical pouch.

6. The system of claim 1, wherein the sterile barrier is a blank medical tray.

7. The system of claim 6, wherein the mounting card includes sidewalls.

8. A hybrid-mounting card to secure medical devices to be placed within a sterile barrier, the hybrid-mounting card comprising
a plurality of receptacles, wherein each receptacle is form fit for a respective portion of a medical device in order to receive and secure the respective portion of the medical device therein, wherein the plurality of receptacles are thermoformed receptacles that include one or more sidewalls, wherein the one or more sidewalls flex apart when pressure is applied to enable the respective portion of the medical device to be received therein and retract back once the respective portion is received to secure the respective portion therewithin; and
a mounting card adapted to receive and secure the plurality of receptacles so as to support the medical device at various pressure points in a defined configuration.

9. The hybrid-mounting card of claim 8, wherein at least one receptacle includes a strap to secure the respective portion of the medical device therein.

10. The hybrid-mounting card of claim 8, wherein the mounting card includes a plurality of openings formed therein to receive the plurality of receptacles.

11. The hybrid-mounting card of claim 8, wherein the mounting card includes slots and the receptacles include a lip and the lip is secured within the slots.

12. The hybrid-mounting card of claim 8, wherein the sterile barrier is a medical pouch.

13. The hybrid-mounting card of claim 8, wherein the sterile barrier is a blank medical tray.

14. A sterile barrier packaging system comprising
one or more thermoformed receptacles, wherein each of the one or more thermoformed receptacles is adapted to receive a respective portion of a medical device and secure the respective portion of the medical device therein, wherein the one or more thermoformed receptacles include one or more sidewalls, wherein the one or more sidewalls flex apart when pressure is applied to enable the respective portion of the medical device to be received therein and retract back once the respective portion is received to secure the respective portion therewithin;
a mounting card adapted to receive and secure the one or more thermoformed receptacles and secure a medical device, wherein the one or more thermoformed receptacles are configured on the mounting card to secure the medical device to the mounting card in a defined configuration and to support the medical device at various pressure points in the defined configuration, wherein the mounting card includes sidewalls;
a blank medical tray to receive the mounting card and the medical device; and
a lid secured to the blank medical tray.

15. The system of claim 14, wherein the mounting card includes one or more openings formed therein to receive the one or more thermoformed receptacles.

16. The system of claim 14, wherein the mounting card includes slots and the one or more thermoformed receptacles each include a lip and the lip is secured within the slots.

17. The system of claim 14, wherein at least one thermoformed receptacle includes a strap to secure the respective portion of the medical device therein.

18. The system of claim 14, wherein the one or more thermoformed receptacles are mounted to the mounting card.

* * * * *